United States Patent [19]

Hart

[11] Patent Number: 5,630,824

[45] Date of Patent: May 20, 1997

[54] SUTURE ATTACHMENT DEVICE

[75] Inventor: Rickey D. Hart, Plainville, Mass.

[73] Assignee: Innovasive Devices, Inc., Hopkinton, Mass.

[21] Appl. No.: 252,444

[22] Filed: Jun. 1, 1994

[51] Int. Cl.$^6$ .................................................. A61B 17/00
[52] U.S. Cl. .................. 606/139; 606/232; 24/136 R; 24/115 M; 24/453
[58] Field of Search ...................... 606/232, 139, 606/151, 158, 228; 24/130, 136 L, 136 R, 136 K, 115 M, 764.1, 453; 128/898

[56] References Cited

U.S. PATENT DOCUMENTS

| | | | |
|---|---|---|---|
| 2,546,534 | 3/1951 | Znidaric | 24/115 X |
| 3,664,345 | 5/1972 | Dabbs et al. | |
| 3,665,560 | 5/1972 | Bennett et al. | |
| 3,766,610 | 10/1973 | Thorsbakken | 24/136 R X |
| 3,845,772 | 11/1974 | Smith | |
| 3,910,281 | 10/1975 | Kletschka et al. | |
| 3,976,079 | 8/1976 | Samuels et al. | |
| 4,059,333 | 11/1977 | Mixon, Jr. | 24/136 R X |
| 4,210,148 | 7/1980 | Stivala | |
| 4,291,698 | 9/1981 | Fuchs et al. | |
| 4,473,102 | 9/1984 | Ohman et al. | 24/136 R X |
| 4,719,671 | 1/1988 | Ito et al. | 24/115 M X |
| 4,750,492 | 6/1988 | Jacobs | |
| 4,834,713 | 5/1989 | Suthanthiran | |
| 5,078,731 | 1/1992 | Hayhurst | |
| 5,193,933 | 3/1993 | Mailey | 24/453 X |
| 5,219,359 | 6/1993 | McQuilkin et al. | |
| 5,236,445 | 8/1993 | Hayhurst et al. | 606/232 |
| 5,258,015 | 11/1993 | Li et al. | |
| 5,268,001 | 12/1993 | Nicholson et al. | |
| 5,269,809 | 12/1993 | Hayhurst | |
| 5,282,832 | 2/1994 | Toso et al. | |
| 5,306,290 | 4/1994 | Martins et al. | |
| 5,324,308 | 6/1994 | Pierce | 606/232 |

FOREIGN PATENT DOCUMENTS

| | | |
|---|---|---|
| 0464480A1 | 6/1991 | European Pat. Off. |
| 0574707A1 | 5/1993 | European Pat. Off. |
| 0592959A3 | 10/1993 | European Pat. Off. |
| 2682867A1 | 10/1991 | France |
| 0 012 360 A1 | 12/1979 | Germany |

*Primary Examiner*—Peter A. Aschenbrenner
*Assistant Examiner*—Michael Peffley
*Attorney, Agent, or Firm*—Choate, Hall & Stewart

[57] ABSTRACT

A suture locking button is described. The device includes a base element with a first axial passage for receiving at least one, and preferably two, suture filaments that is attached via a frangible membrane to a locking dement. The locking dement is adapted for movement from a first position, where the locking element extends outwardly from the base dement, to a second position, where the locking element is disposed within the base element by disrupting the frangible membrane to trap the suture filament(s) within the first axial passage between the locking element and the base element. The locking element may have a flange integral with its proximal end that effectively prevents the base element from backing out of the tissue in a direction proximal to the tissue. The invention also pertains to the combination of a suture and a device for securing the suture to a tissue. A method for securing tissue by way of a suture is also included within the scope of the invention.

18 Claims, 2 Drawing Sheets

SUTURE ATTACHMENT DEVICE

BACKGROUND OF THE INVENTION

The invention relates to the field of surgical devices. At present, in order to close incisions into a human or an animal, both permanent and retention sutures are used. In particular, procedures involving repair of tears to knee and shoulder cartilages, the torn cartilage may be sewn together or affixed to bone.

The sutures in these, and other, surgical procedures are typically held in place by a knot or by conventional suture attachment devices in combination with one or more tissue fasteners. Many conventional suture attachment devices are complex and involve manipulating multi-component systems within a small surgical space. Another problem associated with the use of conventional suture attachment devices is that many of them only operate with a single suture filament and offer a limited degree of tension between the tissue members and/or between tissue members and bone.

SUMMARY OF THE INVENTION

It is therefore one object of the present invention to provide a suture attachment device that may be used with more than one suture filament and which is simple to operate.

It is a further object of the invention to provide a suture attachment device that may be used with sutures of different sizes and which is absorbable by the body.

The present invention is a device for locking a suture to a tissue. One embodiment of the invention includes a base element having a proximal surface and a distal surface with a first axial passage defined between the proximal and distal surfaces for receiving at least one, and preferably more, suture filaments. A locking element having proximal and distal ends is engaged with the base element. The locking element is adapted for movement from a first position, where the locking element is engaged with the proximal surface of the base element and extends outwardly from the base element, to a second position, where the locking element is disposed within the first axial passage to trap the suture filament(s) within the first axial passage between the locking element and the base element. In preferred embodiments, the locking element has a second passage defined in a peripheral wall. This second passage is in communication with the first passage to allow translational movement of the device with respect to the suture filament(s) when the locking element is in the first position. The second passage terminates in an aperture defined in a peripheral wall of the locking element and is preferably disposed at an acute angle with respect to a longitudinal axis of the locking element.

A key feature of the present device is the presence of a frangible membrane that connects the proximal surface of the base and the distal end of the locking elements to each other. This frangible membrane may be substantially annular in shape extending completely around the distal end of the locking element. In other embodiments, the membrane may not be continuous and may include discrete frangible membranes separated by non-frangible portions. The frangible membrane is adapted to break when the locking element is moved from the first to the second position by a force substantially parallel to a longitudinal axis of locking element and substantially orthogonal to a radial axis of the base element.

A suture retention device therefore may include a base having a proximal surface, a distal surface and an internal passage extending from the distal surface through the base to the proximal surface. A locking element having a proximal end, a distal end, and sides connecting said ends is connected to the base via a frangible membrane connecting the proximal surface of the locking element to the distal surface of the base. The frangible membrane has at least one aperture through which a suture can pass. The device is constructed such that the locking element is moveable from a first position in which it is oriented over the passage and a second position in which it is frictionally engaged within the passage, movement of the locking element from its first position to its second position resulting in breakage of the frangible membrane and frictional trapping of any sutures passing through the aperature in the frangible membrane. The sutures are trapped between sides of the locking element and the interior surface of the passage.

In another embodiment, the locking element has a flange integral with its proximal end that extends radially outwardly therefrom. The flange is arranged so that, when the locking element is in the second position, the flange is engaged with the proximal surface of the base element. This effectively prevents the base element from backing out of the tissue in a direction away from the tissue. The flange may further have defined in it at least one groove for receiving a suture filament.

The invention also pertains to the combination of a suture and a device for securing the suture to a tissue. The combination includes a flexible suture; a base element with proximal and distal surfaces and having a passage defined between the surfaces for receiving the suture; a locking element engaged with the base element, the locking element adapted for movement from a first position, where a distal end of the locking element is engaged with the proximal surface of the base element, to a second position, where at least the distal end of the locking element is disposed within the first passage to trap the suture within the passage between the locking element and the base element; and a frangible membrane connecting the locking and base elements that breaks when the locking element moves from the first to the second poisitions.

A method for securing tissue by way of a suture is also included within the scope of the invention. The method includes the steps of passing a suture through the tissue; engaging the suture with a device having a base element engaged by way of a frangible membrane to a locking element, the base and locking elements each having a passage defined through them permitting the device to move along the suture. The device is then moved relative to the suture until the base element contacts the tissue. The locking element is then disposed within the base element by disrupting the frangible membrane so that the suture is trapped between the locking element and the base element.

DETAILED DESCRIPTION OF THE INVENTION

Figure 1:
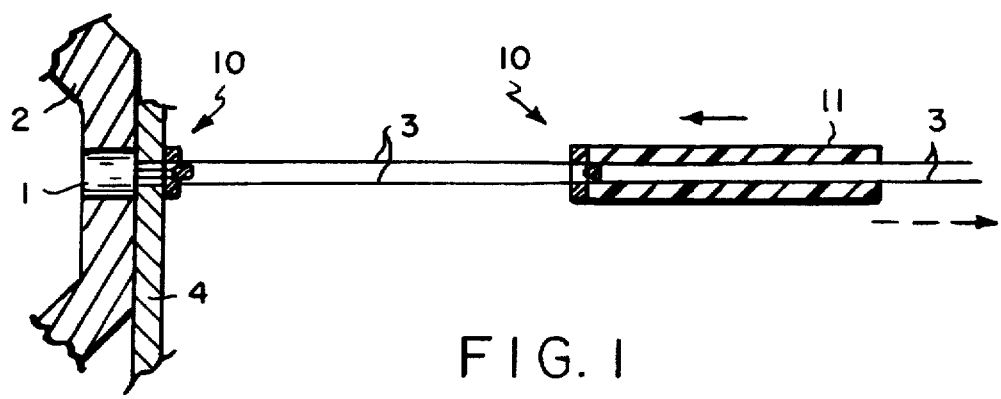
FIG. 1 is a schematic illustration of the relationship between the suture attachment device of the present invention, a suture filament, soft tissue and bone.

FIG. 1 shows general configuration of the invention in which a fastener 1 is embedded in a bone 2. Extending from the proximal end of the fastener 1 is a suture filament 3 which passes through soft tissue 4 and extends proximally, i.e., outwardly and away, from the soft tissue. Generally, the suture filament 3 will contain two separate strands, as illustrated in FIG. 1, although the device of the present invention is designed to utilize any number of suture filaments, as described in more detail below. The suture filament 3 passes through the suture attachment device 10.

An emplacement tool 11 is employed which drives the suture attachment device 10 along the filament 3 (in the direction of the solid arrow) until the attachment device 10 comes into contact with the tissue 4. Tension may be applied to the filament by pulling on it in the direction of the dotted arrow. When the appropriate degree of tension is developed, the emplacement tool 11 is operated to lock the filament 3 to the suture attachment device 10. The filament may be cut or tied off once it is locked. Fastener 1 may be of any type but is preferably of the type described and claimed in U.S. Pat. No. 5,268,001 and may be deployed in a bone using a tool and accessories such as those described in that patent, incorporated herein by reference.

Figure 2:
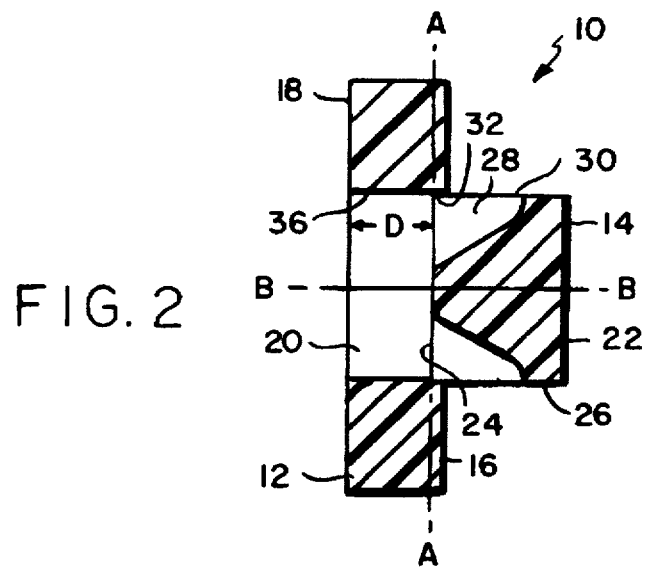
FIG. 2 is a cross-sectional view of a first embodiment of the present invention.
Figure 3:
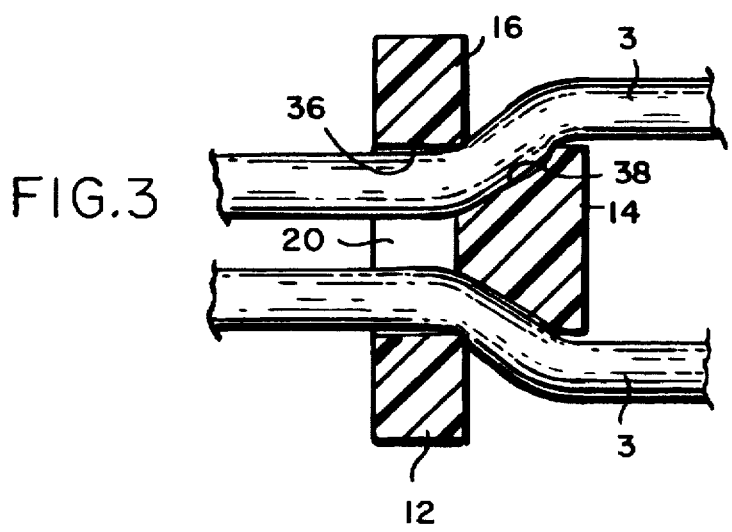
FIG. 3 is a cross-sectional view of the first embodiment in its suture locking position.

Referring to FIGS. 2 and 3, a suture attachment device 10 of the invention includes a base element 12 attached to a locking element 14. Locking element 14 extends in a direction (axis line B—B) substantially perpendicular to a radial axis (lines A—A) of the base element 12. The base element 12 includes a proximal surface 16 (that surface furthest away from the tissue—which is not shown) and a distal surface 18 (i.e., that surface closest to, or in contact with the tissue). Defined between the distal 18 and proximal 16 surfaces is a first passage 20 that is constructed and arranged to receive a suture filament 3. The first passage has a certain depth (D).

Locking element 14 has proximal 22 and distal 24 ends. In particular, the distal end 24 is engaged with the proximal surface 16 of the base element 12 and with the interior of the first passage 20 by way of a frangible membrane 32 (i.e. a membrane capable of being broken or otherwise disrupted), as described in more detail below. In the embodiment illustrated, a peripheral wall 26 of the locking element 14 has defined in it a second passage 28 that is in communication with the first passage 20. The first and second passages 20, 28 together allow for translational movement of the device 10 with respect to the suture filament 3. The second passage 28 is generally formed at an acute angle (i.e., less than ninety degrees and preferably about thirty to about sixty degrees) with respect to the longitudinal axis (B—B) of the locking element 14. The second passage 28 terminates in a aperture 30 that is defined partly in the peripheral wall 26 of the locking element 14 and partly in the frangible membrane 32, this aperture extending from a position adjacent the distal end 24 of the locking element 14 to a position remote from the proximal end 22 of the locking element 14. Most preferably, the size of this aperture and of the second passage 28 is slightly greater than the outside diameter of the particular suture filament that is designed to be locked into the tissue to allow for translational movement of the device along the suture filament. In the embodiment illustrated in FIG. 2, there are two passages 28 defined in the locking element 14, although the number of passages is not intended to limit the scope of the invention in any way. Therefore, there may be a plurality of passages defined in the peripheral wall of the locking element designed to accommodate three or more suture filaments.

Figure 4:
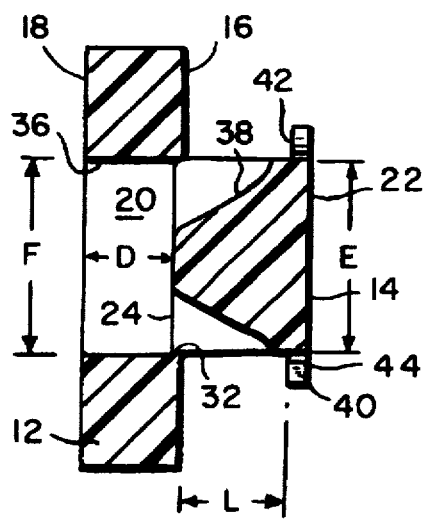
FIG. 4 is a cross-sectional view of a second embodiment of the present invention.
Figure 5:
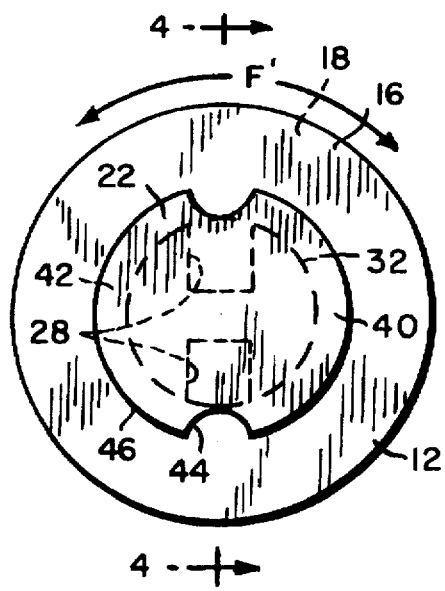
FIG. 5 is a top view of the embodiment of FIG. 4.

FIG. 4 shows another embodiment of the suture attachment device 10. The proximal end 22 of the locking element 14 terminates in a flange 40 that extends radially outward from the proximal end. Flange 40 is arranged so that, when the locking element is in a locked position, a distal surface 42 of the flange 40 is engaged with the proximal surface 16 of base element 12. This locks the base element 12 even more firmly to the filament(s) and prevents any movement of the base element in a direction proximal to the tissue, i.e., towards the surface of the body. FIG. 5 illustrates further a plurality of grooves 44 defined in the outer peripheral edge 46 of this flange 40. Grooves 44 are intended to engage the suture filaments 3 to provide a smooth profile as the suture attachment device is inserted by the surgeon with a minimum of tissue disruption or deformation.

A key feature of the present invention is the means by which the locking and base elements 14, 12 are affixed to each other. Referring again to FIG. 4, the outside diameter (E) of the locking element 14 is slightly smaller than the inside diameter (F) of passage 20 defined in the base element 12. The connection between base element and locking element is made by way of a undercut, thin-walled frangible membrane 32 that joins the distal end 24 of the locking element 14 to the proximal surface 16 of the base element 12. The frangible membrane 32 may be substantially annular and extend completely around distal end 24 of locking element 14. The locking element 14 has a length (L) that is may be substantially equal to the depth (D) of passage 20 defined in the base element 12.

In other embodiments, the frangible membrane is not continuous but rather includes discrete frangible portions that are separated by non-frangible sections. That is, the frangible membrane may be other than a complete annulus of frangible material. In the cross-sectional view of FIG. 5, frangible membrane 32 is a series of spokes or webbing. In this configuration, only the spokes need be broken. Alternately, the frangible membrane may include a plurality of very attenuated membranes.

The device 10 is preferably constructed of a biocompatible material. The term "biocompatible" means that the material is chemically and biologically inert. Suitable materials include, for example, an implant grade high density polyethylene, low density polyethylene (PE 6010 and PE 2030) and polypropylene (13R9A and 23M2: all made by Rexene, Dallas, Tex.). Of these, PE 6010 and 13R9A have been FDA listed as class 6 materials.

The device may also be bioabsorbable. The term "bioabsorbable" refers to those materials that are meant to be decomposed or degraded by bodily fluids, such as, for example, blood and lymph. The device may be made from a biodegradable polymer or copolymer of a type selected in accordance with the desired degradation time. That time in turn depends upon the anticipated healing time of the tissue which is the subject of the surgical procedure. Known bioabsorbable polymers and copolymers range in degradation time from about 3 months for polyglycolide to about 48 months for polyglutamic-co-leucine. A common bioabsorbable polymer used in absorbable sutures is poly (L-lactide) which has a degradation time of about 12 to 18 months. The preferred device is comprised of an absorbable copolymer derived from glycolic and lactic acids, such as a synthetic polyester chemically similar to other commercially available glycolide and lactide copolymers. Glycolide and lactide degrade and absorb in the body by hydrolysis into lactic acid and glycolic acid which are then metabolized by the body.

The following Table set forth below lists polymers which are useful for the bioabsorbable material employed for the device. These polymers are all biodegradable into water-soluble, non-toxic materials which can be eliminated by the body. Their safety has been demonstrated and they are listed as approved materials by the U.S. Food and Drag Administration.

TABLE

Polycaprolactone
Poly (L-lactide)
Poly (DL-lactide)
Polyglycolide
95:5 Poly (DL-lactide-co-glycolide)
90:10 Poly (DL-lactide-co-glycolide)
85:15 Poly (DL-lactide-co-glycolide)
75:25 Poly (DL-lactide-co-glycolide)
50:50 Poly (DL-lactide-co-glycolide)
90:10 Poly (DL-lactide-co-caprolactone)
75:25 Poly (DL-lactide-coocaprolactone)
50:50 Poly (DL-lactide-co-caprolactone)
Polydioxanone
Polyesteramides
Copolyoxalates
Polycarbonates
Poly (glutamic-co-leucine)

As an illustration of the size of the suture in a typical application, a Number 2 braided Dacron synthetic suture filament will have a diameter of about 0.55 mm and the first passage will have a diameter of about 1.2 min. The base element is about 6 mm in diameter and about 1.2 mm thick. The locking element is also about 1.2 mm long. The size of the suture attachment device of the present invention will, however, vary depending on the application and surgical procedure. For example, base element 12 is generally disk-shaped but may be in any shape, i.e., oval, square, rectangular, and the like. As another example of the relative dimensions of the suture attachment device, the device of FIG. 4 may have a base element about 7 mm in diameter and a first passage 3.1 mm in diameter and 1.5 mm deep. The locking element is 3.0 mm in diameter, about 3.5 mm long and terminates in a flange about 4 mm across. Any grooves defined in this flange are about 1 mm in diameter. The internal diameter of the second passage(s) is about 1.2–1.3 mm.

Suture attachment devices of the present invention are made generally by conventional injection molding techniques.

FIGS. 1–3 illustrate use of the suture attachment device 10. The device is placed on the suture filament 3, threading the ends of the suture filament through the first and second passages 20, 28 (see FIGS. 1 and 3). This allows the suture attachment device 10 to slide along the filaments until the distal surface 18 of the base element 12 comes into contact with the tissue 4. The proximal end 22 of the locking element 14 contains a recess (not shown) against which a tool 11 is brought to bear. FIG. 2 shows the device in its first position in which the locking element 14 extends proximally from surface 16 of the base element 12 in a substantially orthogonal direction. The frangible membrane 32 is adapted to break when the locking element is moved from its first position to a second position by a translational force that is substantially parallel to the longitudinal axis (B—B) of locking element 14 (i.e., substantially orthogonal to the radial axis A—A of base element 12). As pressure is applied against proximal end 22 of locking element 14 in this direction, the frangible membrane 32 will break and at least the distal end of locking element 14 will be driven directly into the first passage 20. Depending on the force and the outside diameter of the suture filament, substantially all of length (L) of the locking element 14 may be disposed into the passage 20 defined in the base element 12.

This second, locking position is illustrated in FIG. 3. Translational movement of the locking element 14 into passage 20 defined in the base element 12 will frictionally trap the suture filament 3 within the base element 12 by locking it between a peripheral wall 36 of passage 20 and a peripheral wall 38 of passage 28. That is, disposing the locking element within the base element by disrupting the frangible membrane will frictionally trap the suture within the coextensive passages 20, 28 between the locking element and the base element.

With regard to embodiments in which the frangible membrane 32 includes a series of attenuated membranes (see FIG. 5), the front-to-rear dimension of each of the membranes is sufficiently thick so that it can withstand the counterforce required to balance the force of urging the suture attachment device along the suture filament(s). But the connection of the frangible membrane 32 between the locking and base elements is thin enough so that, with the base element fully engaged with the tissue, the locking element can be rotated about its long axis (B—B) as indicated by arrow F in FIG. 5, to snap off the connections, disposing the locking element into the base element and trapping the suture between the base and locking elements.

One complete method, although by no means the only method, for attaching soft tissue to bone will be described below with reference to the suture attachment device of the present invention and the bone fastener described in U.S. Pat. No. 5,268,001. To attached soft tissue to bone, a surgeon takes the sharpened proximal end of a K-wire (manufactured, for example, by Kirschner Medical Company) and spears the tissue that is to be attached. The proximal end of the K-wire is then placed over the bone surface at the approximate site of attachment. The K-wire is then drilled into the bone at that site. If the location is where the surgeon wants it, the surgeon then threads a cannulated drill of the appropriate size over the K-wire. A hole is then drilled into the bone using the cannulated drill. Then drill is then removed, leaving the K-wire in place. The bone fastener containing a suture then loaded into an emplacement apparatus (described in U.S. Pat. No. 5,268,001, incorporated herein by reference). The fastener containing a suture is run over the K-wire and the fastener pressed downwards through the tissue and into the bone hole and emplaced into the bone hole. If the surgeon decides that the orientation of the bone fastener and soft tissue is correct, the emplacement apparatus is triggered to set the bone fastener within the bone hole. The emplacement apparatus and then the K-wire are removed in turn. Other variations on this technique include first drilling a bone hole and then punching a hole through the soft tissue. The tissue is then moved over the bone hole using, for example, a K-wire or a grasping device. The K-wire is inserted into the hole in the soft tissue and bone and then the emplacement apparatus threaded over the K-wire.

The suture attachment device 10 of the present invention is then threaded onto the suture filament(s) protruding from the soft tissue, and the suture locking mechanism of the present device is activated as described.

Figure 6:
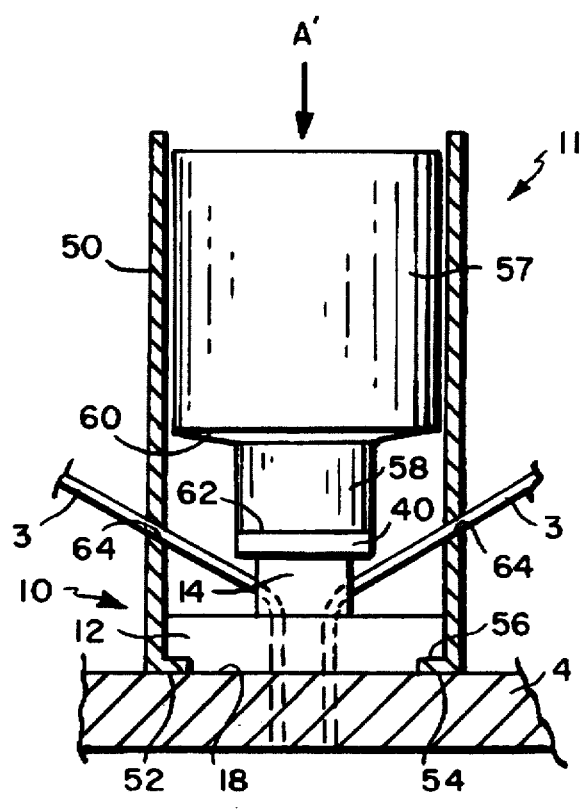
FIG. 6 is a schematic, cross-section of the suture attachment device of FIG. 4 engaged with an emplacement tool.

FIG. 6 illustrates a schematic cross-section of the suture attachment device 10 in place within an emplacement tool 11. The distal surface 18 of the base element 12 is engaged with tissue 4 and two suture filaments 3 protrude from the locking element 14. Device 10 is inside a hollow, elongated holder 50. A distal end 52 of holder 50 has one or more projections 54 that engage with the distal surface 18 of base element 12. In FIG. 6, the distal surface 18 includes one or more detents 56 that mate with their corresponding projections to maintain the device 10 securely within the holder. Holder 50 may be made of metal or plastic. If made of plastic, the holder may be injection molded as a one-piece unit along with device 10. In this case, the distal attachment of holder 50 to the base element 12 may be by way of a frangible membrane (not shown), rather than a series of projections 54.

A plunger 57 is engaged co-axially within holder 50. A projection 58 on distal end 60 of the plunger is designed to mate with the proximal end of the locking element 14. In the particular embodiment illustrated, distal end 58 of plunger 57 engages the proximal surface 62 of flange 40 on locking element (see also FIG. 4). The two suture filaments 3 are threaded through corresponding apertures 64 in the holder 50. Alternately, the two suture filaments 3 may pass entirely through the body of the holder. In use, pressure is applied on the plunger in the direction of arrow A. The frangible membrane (not shown) connecting base and locking elements is designed to withstand enough force so that the membrane breaks while the device is within the holder, thus locking the suture filaments to the device before the device is released from the holder. Movement of the plunger is continued to release the device from the holder. It will be understood by those of ordinary skill in the art that the net force on the tissue is approximately zero. To avoid premature deployment of the device, the holder 50 and device 10 are engaged with each other so that any force required to release the device from the holder is greater than the force needed to break the frangible membrane connecting the base and locking elements. In this way, the device is released from the holder only after the locking element is driven into the base element.

The suture attachment device described herein is of particular utility in the repair and reattachment of soft tissues or bone to bone. Specifically, repair of the anterior cruelate ligament of the knee has been accomplished in the past by removing a portion of the patella tendon and a bone block from the patella and the tibia. The bone block is then sized according to fit into a blind hole in the head of the femur and through a hole in the head of the tibia and are fixed in the holes typically with screws. However, before the bone blocks are fit into their respective holes, sutures are placed through one of the bone blocks that will fit into the tibia and are secured to the tibia using screws or staples outside of the hole in the tibia. The sutures apply tension to the cruciate ligament while fixing the bone block in the tibia with screws. When affixing the bone block in the tibia, the sutures are held in tension, to the surgeon's preference. Installation of the screw causes the tibia bone block to move relative to the pretensioned placement achieved by the surgeon. This movement causes the surgeon to over-, or undercompensate for movement of the bone block relative to the tibia.

The suture attachment device described herein will eliminate the need for a screw or staple into the head of the tibia, allowing for better placement of the bone block in the tibia. It will also remain flush with the tibia hole, eliminating any objects under the skin that may be noticeable postoperatively. The suture filament emanating from the head of the tibia may be conveniently locked using the device of the present invention.

EQUIVALENTS

It will be understood that the preceding is merely a description of certain preferred embodiments of the present invention. It will be readily apparent to one of ordinary skill in the art that various modifications can be made without departing from the spirit or scope of the invention. Modifications and equivalents are therefore within the scope of the invention.

I claim:

1. A device for locking a suture to a tissue, comprising:
   a base element having a proximal surface and a distal surface, the base element having defined between the distal and proximal surfaces a first axial passage for receiving a suture; and
   a locking element engaged with the base element and having:
   a peripheral wall having defined therein a second passage terminating in an aperture defined in the peripheral wall for receiving the suture from the first passage; and
   proximal and distal ends defining a longitudinal axis, wherein the locking element is adapted for movement along the longitudinal axis from:
   a first position, in which the locking element is engaged with the proximal surface of the base element and can move in a proximal-distal direction relative to the suture threaded through the first and second passages; to
   a second position, in which the locking element is disposable within the first passage by a force acting parallel to the longitudinal axis and parallel to the suture received within the first passage, so as to trap the suture between the locking element and the base element.

2. The device of claim 1, wherein the locking element extends from a proximal surface of the base element.

3. The device of claim 1, wherein the second passage is disposed at an acute angle with respect to the longitudinal axis of the locking element.

4. The device of claim 1, wherein the locking element is affixed to the base element by way of a frangible membrane.

5. The device of claim 4, wherein the frangible membrane is adapted to break when the locking element is moved from the first to the second positions.

6. The device of claim 1, wherein the aperture in the peripheral wall of the locking element extends from the frangible membrane to a position remote from the proximal end of the locking element.

7. The device of claim 1, wherein the locking element is substantially orthogonal to the base element.

8. The device of claim 7, wherein the locking element is centrally located on the proximal surface of the base element.

9. A device for locking a suture to a tissue, comprising:
   a base element having a proximal surface and a distal surface for engagement with a surface of the tissue, the base element having defined between its distal and proximal surfaces a first axial passage for receiving a suture emanating from the tissue surface;
   a locking element having proximal and distal ends defining a longitudinal axis, the distal end of the locking element connected to the proximal end of the base element by way of a frangible membrane, the locking element further including a peripheral wall having defined therein a second passage in communication with the first passage, the first and second passages for allowing the suture to enter the base element and extend in a proximal direction through the first and second passages;

a flange integral with the proximal end of the locking element and extending radially outwardly therefrom, wherein the locking element is adapted for movement from a first position, where the locking element is engaged with the proximal surface of the base element, to a second position, where the locking element is disposed within the first passage to trap the suture between the locking element and the base element, the flange arranged so that, when the locking element is in the second position, the flange is engaged with the proximal end of the base element to prevent movement of the base element in a direction proximal to the tissue.

10. The device of claim 9, wherein the flange further has defined therein at least one groove for receiving a suture.

11. The device of claim 10, wherein the groove is defined in an outer edge of the flange.

12. In combination, a suture and a device for securing the suture to a tissue, the combination comprising:

a flexible suture filament;

a base element with proximal and distal surfaces and having a first passage defined therethrough for receiving the suture filament;

a locking element engaged with the base element and having a second passage defined therethrough for receiving the suture filament from the first passage; and a frangible membrane connecting the locking and base elements, wherein the locking element is adapted for movement, in a direction substantially parallel to the suture, from a first position where a distal end of the locking element is engaged with the proximal surface of the base element, to a second position, where the frangible membrane is disrupted and the locking element is disposed within the first passage to trap the suture filament between the locking element and the base element.

13. A suture retention device comprising:

a base having a proximal surface, a distal surface and a first internal passage extending from the distal surface through the base to the proximal surface;

a locking element having a proximal end, a distal end, sides connecting the ends and a second passage defined in a peripheral wall of the locking element, the second passage in communication with the first internal passage of the base, the first and second passages allowing a suture to pass therethrough in a proximal-distal direction; and a frangible membrane connecting the proximal surface of the locking element to the distal surface of the base so that the locking element is moveable from a first position, in which the locking element is oriented over the first internal passage of the base, to a second position in which the locking element is frictionally engaged within the first internal passage of the base, wherein movement of the locking element in a direction parallel to the suture from the first position to the second position, breaks the frangible membrane and frictionally traps between the sides of the locking element and the interior surface of the first internal passage, any suture passing in a proximal-distal direction through the first and second passages.

14. A method for securing tissue with a suture, comprising:

passing a suture filament through the tissue;

engaging the suture filament with a device having a base element for contacting the tissue, and a locking element connected to the base element by way of a frangible membrane, the base and locking elements each having a passage defined through them that are interconnected, the passages permitting the device to move along the suture in a proximal-distal direction;

moving the device in a proximal-distal direction relative to the suture until the base element contacts the tissue;

disposing the locking element within the base element by disrupting the frangible membrane with a force in the proximal-distal direction so that the suture is trapped between the locking element and the base element.

15. The method of claim 14, wherein the step of engaging comprises engaging with a first and a second passage of the device of claims 1 or 12.

16. The method of claim 14, wherein the step of engaging comprises engaging with a first and a second passage of the device of claim 9.

17. A device for locking a suture to a tissue, comprising:

a base element having a proximal surface and a distal surface, the base element having defined between the distal and proximal surfaces a first axial passage for receiving a suture, wherein the first passage is of substantially uniform cross-section;

a locking element engaged with the base element and having proximal and distal ends defining a longitudinal axis, wherein the locking element is adapted for movement along the longitudinal axis from a first position, where the locking element is engaged with the proximal surface of the base element, to a second position, where the locking element is disposable within the fast passage by a force acting parallel to the longitudinal axis and parallel to the suture received within the fast passage, so as to trap the suture between the locking element and the base element.

18. A device for locking a suture to a tissue, comprising:

a base element having a proximal surface and a distal surface, the base element having defined between the distal and proximal surfaces a first axial passage for receiving a suture;

a frangible membrane including discrete frangible membranes separated by non-frangible portions, wherein the frangible membrane affixes the base element to a locking element;

a locking element having proximal and distal ends defining a longitudinal axis, wherein the locking element is adapted for movement along the longitudinal axis from:

a first position, in which the locking element is engaged with the proximal surface of the base element, and to:

a second position, in which the locking element is disposable within the first passage by a force acting parallel to the longitudinal axis and parallel to the suture received within the fast passage, so as to trap the suture between the locking element and the base element.

* * * * *

UNITED STATES PATENT AND TRADEMARK OFFICE
CERTIFICATE OF CORRECTION

PATENT NO. : 5,630,824
DATED : May 20, 1997
INVENTOR(S) : Rickey D. Hart

It is certified that error appears in the above-indentified patent and that said Letters Patent is hereby corrected as shown below:

In the "Abstract", please delete any instance of the word "dement"; and insert therefor --element--.

Column 5, line 31: please delete "min."; and insert therefor --mm.--.

Column 7, line 42: please delete "cruelate"; and insert therefor --cruciate--.

Column 10, line 37: please delete "fast"; and insert therefor --first--.

Column 10, line 39: please delete "fast"; and insert therefor --first--.

Column 10, line 60: please delete "fast"; and insert therefor --first--.

Signed and Sealed this

Fifth Day of August, 1997

*Attest:*

BRUCE LEHMAN

*Attesting Officer*    Commissioner of Patents and Trademarks